US007720783B2

(12) United States Patent
Staddon et al.

(10) Patent No.: US 7,720,783 B2
(45) Date of Patent: May 18, 2010

(54) METHOD AND SYSTEM FOR DETECTING UNDESIRED INFERENCES FROM DOCUMENTS

(75) Inventors: Jessica N. Staddon, Redwood City, CA (US); Philippe J. P. Golle, San Francisco, CA (US); Bryce D. Zimny, Oshawa (CA)

(73) Assignee: Palo Alto Research Center Incorporated, Palo Alto, CA (US)

( * ) Notice: Subject to any disclaimer, the term of this patent is extended or adjusted under 35 U.S.C. 154(b) by 484 days.

(21) Appl. No.: 11/729,576

(22) Filed: Mar. 28, 2007

(65) Prior Publication Data

US 2008/0243825 A1 Oct. 2, 2008

(51) Int. Cl.
*G06F 17/00* (2006.01)
*G06N 5/02* (2006.01)

(52) U.S. Cl. .......................................... 706/46; 706/45

(58) Field of Classification Search ............ 706/45-48; 707/100

See application file for complete search history.

(56) References Cited

U.S. PATENT DOCUMENTS 6,246,977 B1 * 6/2001 Messerly et al. ............... 704/9
7,031,969 B2 * 4/2006 Lawrence et al. ........... 707/100

OTHER PUBLICATIONS

Yu Chen and Wesley W. Chu, "Database Security Protection Via Inference Detection", S. Mehrotra et al. (Eds.): ISI 2006, LNCS 3975, pp. 452-458, 2006.*

"Natural Language Processing for Information Assurance", by Mikhail Atallah et al., Proc. 9$^{th}$ ACM/SIGSAC New Security Paradigms Workshop, 2000, pp. 51-65.

"Mining Email Content for Author Identification Forensics", by O.de Vel et al., SIGMOD Record, vol. 30, No. 4, Dec. 2001.

"Factiva Insight: Reputation Intelligence", http://www.factiva.com.

Fetch Technologies, http://fetch.com.

"Community Search Assistant", by Natalie S. Glance, IUI, 2001.

"The Myth of the Double-Blind Review? Author Identification Using Only Citations", by S. Hill et al., SIGKDD Explorations, 2003.

"Using the Web as an Implicit Training Set: Application to Structural Ambiguity Resolution", by Preslav Nakov et al., HLT-NAACL, 2005.

(Continued)

*Primary Examiner*—David R Vincent
*Assistant Examiner*—Vincent M Gonzales
(74) *Attorney, Agent, or Firm*—Park, Vaughan & Fleming LLP; Shun Yao

(57) ABSTRACT

One embodiment of the present invention provides a system that detects inferences from documents. During operation, the system receives one or more documents and extracts a first set of knowledge relevant to the documents. The system further formulates one or more queries to one or more reference corpora based on the first set of knowledge. The system then extracts a second set of knowledge from results received in response to the queries. Additionally, the system produces a mapping relationship between at least one document and a piece of the second set of knowledge which is not within the first set of knowledge, the mapping relationship indicating an inference from the documents.

25 Claims, 7 Drawing Sheets

OTHER PUBLICATIONS

"AI Technologies to Defeat Identity Theft Vulnerabilities", by L. Sweeney, AAAI Spring Symposium on AI Technologies for Homeland Security, 2005.

Hale J. et al: "Catalytic inference analysis: detecting inference threats due to knowledged discovery", Security and Privacy, 1997. Proceedings., 1997 IEEE Symposium on Okland, CA, USA May 4-7, 1997, Los Alamitos, CA, USA, IEEE Comput. Soc, US, May 4, 1997, pp. 188-199, XP010230155, ISBN:978-0-8186-7828-8.

Frakas C. et al: "The inference problem: 1-12 a survey", ACM SIGKDD Explorations Newsletter, (online), vol. 4, No. 2, Dec. 2002, pp. 6-11, XP002495620, ISBN:1931-0145, URL: http://doi.acm.org/10.1145/772862.772864>.

Chen, Yu et al: "Database Security Protection Via Inference Detection" Intelligence and Security Information Lecture Notes in Computer Science ;; LNCS, Springer; Berlin, DE, vol. 3975, Jan. 1, 2006, pp. 452-458, XP019033806, ISBN: 978-3-540-34478-0.

Gauch et al: "A Corpus Analysis Approach for Extension to Multiple Databases" ACM, Transactions on Information Systems, ACM, New York, NY, US, vol. 17, No. 3, Jul. 1, 1999, ISSN: 1046-8188.

* cited by examiner

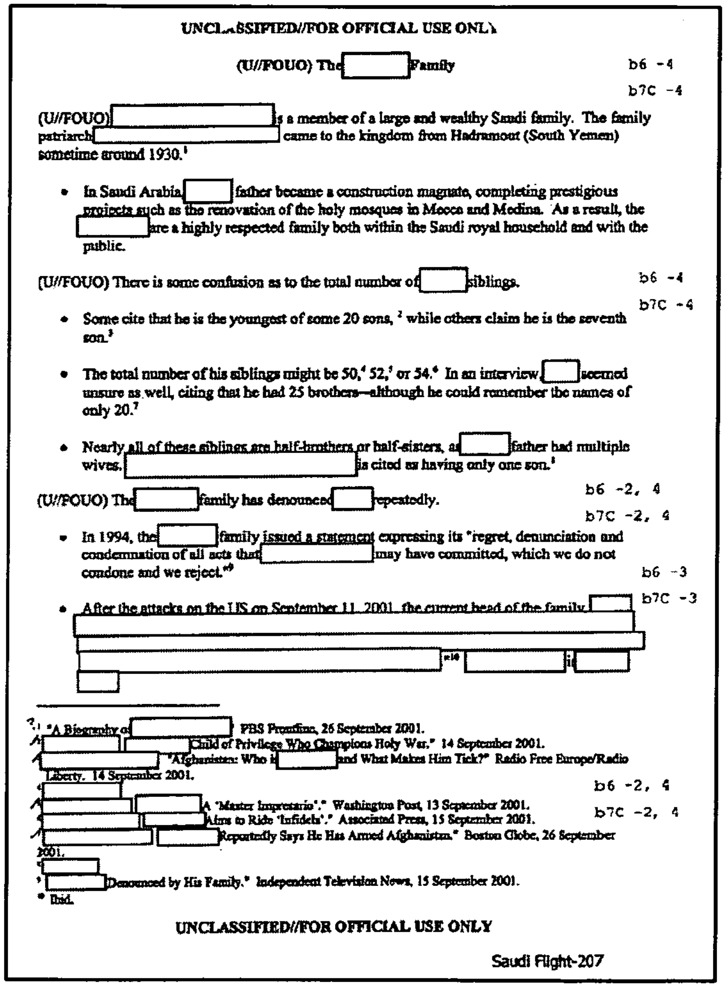

UNCLASSIFIED//FOR OFFICIAL USE ONLY (U//FOUO) The Family b6 -4 b7C -4

(U//FOUO) is a member of a large and wealthy Saudi family. The family patriarch came to the kingdom from Hadramout (South Yemen) sometime around 1930.[1]

- In Saudi Arabia, father became a construction magnate, completing prestigious projects such as the renovation of the holy mosques in Mecca and Medina. As a result, the are a highly respected family both within the Saudi royal household and with the public.

(U//FOUO) There is some confusion as to the total number of siblings. b6 -4 b7C -4

- Some cite that he is the youngest of some 20 sons,[2] while others claim he is the seventh son.[3]
- The total number of his siblings might be 50,[4] 52,[5] or 54.[6] In an interview, seemed unsure as well, citing that he had 25 brothers—although he could remember the names of only 20.[7]
- Nearly all of these siblings are half-brothers or half-sisters, as father had multiple wives. is cited as having only one son.[8]

(U//FOUO) The family has denounced repeatedly. b6 -2, 4 b7C -2, 4

- In 1994, the family issued a statement expressing its "regret, denunciation and condemnation of all acts that may have committed, which we do not condone and we reject."[9] b6 -3 b7C -3
- After the attacks on the US on September 11, 2001, the current head of the family [10]

[1] "A Biography of PBS Frontline, 26 September 2001.
"Child of Privilege Who Champions Holy War." 14 September 2001.
"Afghanistan: Who and What Makes Him Tick?" Radio Free Europe/Radio Liberty. 14 September 2001.
b6 -2, 4 b7C -2, 4
"Master Impresario'." Washington Post, 13 September 2001.
Aims to Ride 'Infidels'." Associated Press, 15 September 2001.
Reportedly Says He Has Armed Afghanistan." Boston Globe, 26 September 2001.
Denounced by His Family." Independent Television News, 15 September 2001.
Ibid.

UNCLASSIFIED//FOR OFFICIAL USE ONLY

Saudi Flight-207

FIG. 1

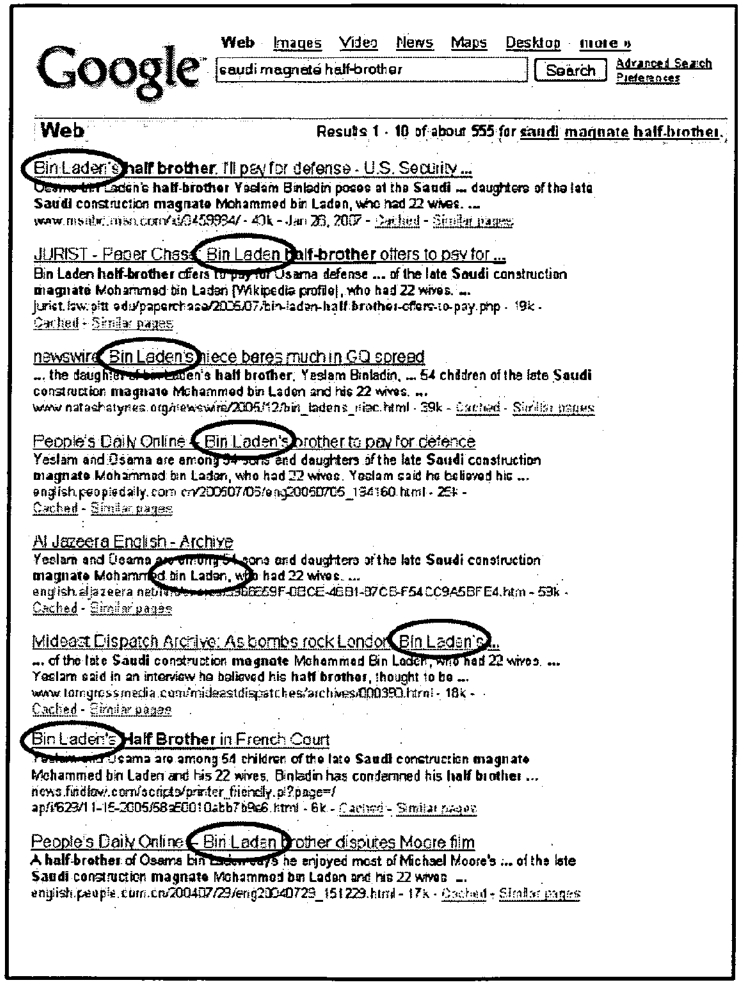

Google Web Images Video News Maps Desktop more »
saudi magnate half-brother Search Advanced Search Preferences Web Results 1 - 10 of about 555 for saudi magnate half-brother.

Bin Laden's half brother: I'll pay for defense - U.S. Security ...
Osama bin Laden's half-brother Yeslam Binladin poses at the Saudi ... daughters of the late Saudi construction magnate Mohammed bin Laden, who had 22 wives. ...
www.msnbc.msn.com/id/16459984/ - 40k - Jan 26, 2007 - Cached - Similar pages JURIST - Paper Chase: Bin Laden half-brother offers to pay for ...
Bin Laden half-brother offers to pay for Osama defense ... of the late Saudi construction magnate Mohammed bin Laden [Wikipedia profile], who had 22 wives. ...
jurist.law.pitt.edu/paperchase/2005/07/bin-laden-half-brother-offers-to-pay.php - 19k - Cached - Similar pages newswire: Bin Laden's niece bares much in GQ spread
... the daughter of bin Laden's half brother, Yeslam Binladin, ... 54 children of the late Saudi construction magnate Mohammed bin Laden and his 22 wives. ...
www.natashatynes.org/newswire/2005/12/bin_ladens_niec.html - 39k - Cached - Similar pages People's Daily Online - Bin Laden's brother to pay for defence
Yeslam and Osama are among 54 sons and daughters of the late Saudi construction magnate Mohammed bin Laden, who had 22 wives. Yeslam said he believed his ...
english.peopledaily.com.cn/200507/05/eng20050705_194160.html - 25k - Cached - Similar pages Al Jazeera English - Archive
Yeslam and Osama are among 54 sons and daughters of the late Saudi construction magnate Mohammed bin Laden, who had 22 wives. ...
english.aljazeera.net/NR/exeres/3B6E59F-0BCE-46B1-87CB-F54CC9A5BFE4.htm - 53k - Cached - Similar pages Mideast Dispatch Archive: As bombs rock London, Bin Laden's ...
... of the late Saudi construction magnate Mohammed Bin Laden, who had 22 wives. ... Yeslam said in an interview he believed his half brother, thought to be ...
www.tomgrossmedia.com/mideastdispatches/archives/000390.html - 18k - Cached - Similar pages Bin Laden's Half Brother in French Court
Yeslam and Osama are among 54 children of the late Saudi construction magnate Mohammed bin Laden and his 22 wives. Binladin has condemned his half brother ...
news.findlaw.com/scripts/printer_friendly.pl?page=/ap/f/623/11-15-2005/58a50010abb7b9e6.html - 6k - Cached - Similar pages People's Daily Online - Bin Laden brother disputes Moore film
A half-brother of Osama bin Laden says he enjoyed most of Michael Moore's ... of the late Saudi construction magnate Mohammed bin Laden and his 22 wives ...
english.people.com.cn/200407/29/eng20040729_151229.html - 17k - Cached - Similar pages

FIG. 2

Summary of STD Experiments

Input Web Page, $B$: Wikipedia STD site [39]

Extracted Keywords, $S_B$: transmit, sexually, transmitting, transmitted, infection, std, sti, hepatitis, infected; infections, transmission, stis, herpes, viruses, virus, chlamydia,_[a], stds, sexual, disease, hiv, membrane, genital, intercourse, diseases, pmid, hpv, mucous, viral, 2006

Input Web Page, $B'$, ("control" page): Medical Terms Site [28]

Extracted "Control" Keywords, $S'_B$: Ablation, Ah-Al, Aneurysm, thoracic, Arteria femoralis, Barosinusitis, Bone mineral density, Cancer, larynx, Chain-termination codon, Cockayne syndrome, Cranial nerve IX, Dengue, Disorder, cephalic, ECT, Errors of metabolism, inborn, Fear of nudity, Fracture, comminuted, Gland, thymus, Hecht-Beals syndrome, Hormone, thyroxine, Immunocompetent, Iris melanoma, Laparoscopic, Lung reduction surgery, Medication, clot-dissolving, Mohs surgery, Nasogastric tube, Normoxia, Osteosarcoma, PCR (polymerase chain reaction), Plan B

**Sensitive Keywords, $K^*_{STD}$**: STD, Chancroid, Chlamydia, Donovanosis, Gonorrhea, Lymphogranuloma venereum, Non-gonococcal urethritis, Syphilis, Cytomegalovirus, Hepatitis B, Herpes, HSV, Human Immunodeficiency Virus, HIV, Human papillomavirus, HPV, genital warts, Molluscum, Severe acute respiratory syndrome, SARS, Pubic lice, Scabies, crabs, Trichomoniasis, yeast infection, bacterial vaginosis, trichomonas, mites, nongonococcal urethritis, NGU, molluscum contagiosm virus, MCV, Herpes Simplex Virus, Acquired immunodeficiency syndrome, aids, pubic lice, HTLV, trichomonas, amebiasis, Bacterial Vaginosis, Campylobacter Fetus, Candidiasis, Condyloma Acuminata, Enteric Infections, Genital Mycoplasmas, Genital Warts, Giardiasis, Granuloma Inguinale, Pediculosis Pubis, Salmonella, Shingellosis, vaginitis

**Percentage of words in $S_B$ yielding a top hit containing word(s) in $K^*_{STD}$**: 33.33%

**Percentage of word pairs in $S_B$ yielding a top hit containing word(s) in $K^*_{STD}$**: 70.34%

**Percentage of "control" words in $S'_B$ yielding a top hit containing word(s) in $K^*_{STD}$**: 3.33%

**Percentage of "control" word pairs in $S'_B$ yielding a top hit containing word(s) in $K^*_{STD}$**: 24.83%

**Example keyword pairs from $S_B$ returning a top hit containing a word in $K^*_{STD}$**:[b]

| Keywords | URL of Top Hit | Sensitive Word in Top Hit |
|---|---|---|
| transmit, infected | http://www.rci.rutgers.edu/ insects/aids.htm | HIV |
| transmit, mucous | http://research.uiowa.edu/animal/?get=empheal | Herpes |
| transmitting, viruses | http://www.cdc.gov/hiv/resources/factsheets/transmission.htm | Hepatitis B |
| transmitted, viral | http://www.eurosurveillance.org/em/v10n02/1002-226.asp | Hepatitis B |
| transmitted, infection | http://www.plannedparenthood.org/sti/ | STD |
| transmitted, disease | http://www.epigee.org/guide/stds.html | STD |
| infection, mucous | http://www.niaid.nih.gov/factsheets/sinusitis.htm | HIV |
| infected, disease | http://www.ama-assn.org/ama/pub/category/1797.html | HIV |
| infected, viral | http://www.merck.com/mmhe/sec17/ch198/ch198a.html | Cytomegalovirus |
| infections, viral | http://www.nlm.nih.gov/medlineplus/viralinfections.html | Cytomegalovirus |
| virus, disease | http://www.mic.ki.se/Diseases/C02.html | Cytomegalovirus |

[a]Note this extracted non-word indicates a flaw in our text-from-html extraction algorithm.

[b]In a manual review of the word pairs from $W'_B$ yielding a top hit containing word(s) in $K^*_{STD}$, we did not find any hits using the word pair in a meaningful way in relation to a sensitive word. Rather, the hits generally turned out to be medical term lists.

FIG. 8

Summary of Alcoholism Experiments

Input Web Page, $B$: Wikipedia Alcoholism site [38]

Extracted Keywords, $S_B$: alcoholism, alcohol, drunk, alcoholic, alcoholics, naltrexone, drink, addiction, dependence, detoxification, diagnosed, screening, drinks, moderation, abstinence, 2006, disorder, drinking, behavior, questionnaire, cage, treatment, citation , acamprosate, because, pharmacological, anonymous, extinction, sobriety, dsm

Input Web Page, $B'$, ("control" page): Medical Terms Site [28]

Extracted "Control" Keywords, $S'_B$: ABO blood group, Alarm clock headache, Ankle-foot orthosis, Ascending aorta, Benign lymphoreticulosis, Breast bone, Carotid-artery stenosis, Chondromalacia patellae, Congenital, Cystic periventricular leukomalacia, Discharge, DX, Enterococcus, Familial Parkinson disease type 5, Fondation Jean Dausset-CEPH, Giant cell pneumonia, Heart attack, Hormone, parathyroid, Impetigo, Itching, Laughing gas, M. intercellulare, Membranous nephropathy, MRSA, Nerve palsy, laryngeal, Oligodendrocyte, Pap Smear, Phagocytosis, Postoperative, Purpura, Henoch-Schonlein

**Sensitive Keywords, $K^*_{Alc}$:** alcoholism, alcoholic(s), alcohol

**Percentage of words in $S_B$ yielding a top hit containing word(s) in $K^*_{Alc}$:** 23.33%

**Percentage of word pairs in $S_B$ yielding a top hit containing word(s) in $K^*_{Alc}$:** 47.82%

**Percentage of "control" words in $S'_B$ yielding a top hit containing word(s) in $K^*_{Alc}$:** 0.00%

**Percentage of "control" word pairs in $S'_B$ yielding a top hit containing word(s) in $K^*_{Alc}$:** 9.43%

**Example word sets from $S_B$ returning a top hit containing a word in $K^*_{Alc}$:**[a]

| Keywords | URL of Top Hit |
|---|---|
| naltrexone | http://www.nlm.nih.gov/medlineplus/druginfo /medmaster/a685041.html |
| acamprosate | http://www.nlm.nih.gov/medlineplus/druginfo /medmaster/a604028.html |
| dsm, detoxification | http://www.aafp.org/afp/20050201/495.html[b] |
| dsm, detoxification, dependence | http://www.aafp.org/afp/20050201/495.html |

[a] Since all of our sensitive words pertain to the same topic, alcoholism, we did not record which particular sensitive word was contained in the top hit (if any).

[b] Note this is the $4^{th}$ returned hit, indicating a change in our search strategy would improve recall.

FIG. 9

METHOD AND SYSTEM FOR DETECTING UNDESIRED INFERENCES FROM DOCUMENTS

BACKGROUND

1. Field of the Invention

The present invention relates to the design of intelligent data processing. More specifically, the present invention relates to a method and system for detecting undesirable inferences that can be drawn from a set of documents.

2. Related Art

The relentless growth of the Internet has made the World Wide Web (the Web) one of the largest and most accessible pool of information today. In response, powerful search engines have emerged to help users locate and retrieve a document of interest on the Web. These search engines are becoming progressively faster, more thorough, and more accurate. It has never been easier to look up facts, keep up with events, and catch up with people with Web-based resources, such as Webpages, blogs, online data repositories, online newspapers, and online public records.

However, these online resources also make protecting information privacy much more difficult. With the help of a search engine or a Web information integration tool, one can easily infer facts, reconstruct events, and piece together identities from fragments of information collected from disparate sources. Therefore, protecting information requires concealing not only the information itself, but also a myriad of clues that might indirectly lead to it. Doing so is notoriously difficult, because seemingly innocuous information may give away one's secret.

Hence, there is a need for a method and a system for detecting undesired inferences to facilitate more effective protection of information privacy.

SUMMARY

One embodiment of the present invention provides a system that detects inferences from documents. During operation, the system receives one or more documents and extracts a first set of knowledge relevant to the documents. The system further formulates one or more queries to one or more reference corpora based on the first set of knowledge. The system then extracts a second set of knowledge from results received in response to the queries. Additionally, the system produces a mapping relationship between at least one document and a piece of the second set of knowledge which is not within the first set of knowledge, the mapping relationship indicating an inference from the documents.

In a variation on this embodiment, extracting the first set of knowledge relevant to the document involves deriving a set of words or phrases relevant to each document.

In a further variation, deriving the set of words or phrases involves determining a term-frequency inverse-document-frequency (TF.IDF) weight for a word or phrase contained in the document.

In a variation on this embodiment, extracting the first set of knowledge involves extracting a set of words or phrases from each document. Furthermore, formulating the queries involves constructing single-word queries, multi-word queries, or both from the extracted words or phrases.

In a further variation, extracting a set of words or phrases from each document involves extracting a pre-determined number of words or phrases from the document.

In a variation on this embodiment, the system retrieves a pre-determined number of results for each query.

In a variation on this embodiment, the system receives a set of sensitive knowledge relevant to the documents. The piece of the second set of knowledge mapped to the document is also within the set of sensitive knowledge. Furthermore, producing the mapping relationship involves determining an intersection between the set of sensitive knowledge and the second set of knowledge.

In a variation on this embodiment, producing the mapping relationship involves presenting one or more words or phrases from the documents, wherein these words or phrases correspond to the first set of knowledge, and one or more sensitive words or phrases extracted from the query results.

In a variation on this embodiment, the system determines a ratio of: the number of results returned by a first query based on one or more words or phrases from the documents and one or more sensitive words or phrases, to the number of results returned by a second query based on one or more words or phrases from the documents. The system further determines an inference from the one or more words or phrases used to generate the first query based on the size of the ratio.

In a variation on this embodiment, the system selects the one or more reference corpora based on the documents, an intended audience, or both.

In a variation on this embodiment, the inference is an undesired inference which can be extracted from a union of the document and the corpus and which cannot be extracted from the document or the corpus alone

BRIEF DESCRIPTION OF THE FIGURES

FIG. 1 illustrates an exemplary redacted public document.

FIG. 2 illustrates exemplary search results from queries based on the published document illustrated in FIG. 1.

FIG. 8 presents a summary of an experiment to identify keywords enabling STD inferences in accordance with one embodiment of the present invention.

FIG. 9 presents a summary of an experiment to identify keywords enabling alcoholism inferences in accordance with one embodiment of the present invention.

Figure 3:
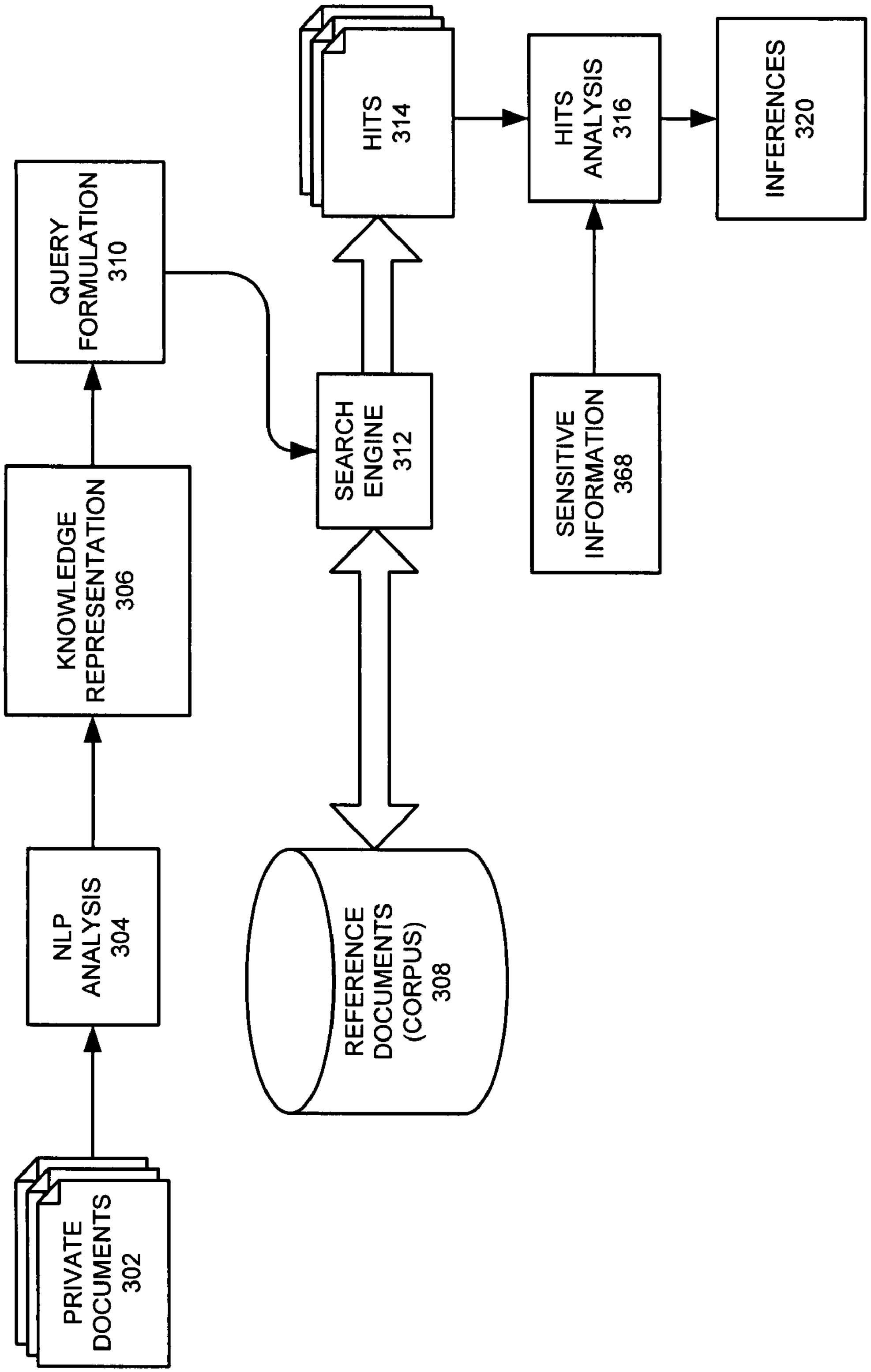
FIG. 3 presents an exemplary block diagram illustrating the process of Web-based inference detection in accordance with an embodiment of the present invention.

TABLE 1 presents excerpts from a de-anonymization experiment based on an inference-detection model in accordance with one embodiment of the present invention.

DETAILED DESCRIPTION

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not limited to the embodiments shown, but is to be accorded the widest scope consistent with the claims.

The data structures and code described in this detailed description are typically stored on a computer-readable storage medium, which may be any device or medium that can store code and/or data for use by a computer system. This includes, but is not limited to, volatile memory, non-volatile memory, magnetic and optical storage devices such as disk drives, magnetic tape, CDs (compact discs), DVDs (digital versatile discs or digital video discs), or other media capable of storing computer readable media now known or later developed.

Overview

Embodiments of the present invention provide a system for detecting undesired inferences from one or more documents. The risk of undesired inferences arises when a private document becomes partially public, and when such partial disclosure allows the public to infer certain information intended to remain private.

To illustrate the problem, consider a redacted biography of Osama Bin Laden released by the FBI, which is shown in FIG. 1 and available at http//www.judicialwatch.org/archive/2005/osama.pdf. Prior to publishing the document, the FBI has redacted the biography to protect the identity of the person. All directly identifying information, such as first and last names, has been expunged from the biography. The redacted document contains only generally applicable words, such as "half-brother," "Saudi," "magnate," and "Yemen." None of these words are particularly identifying on their own, but in aggregate these words allow for near-certain identification of Osama Bin Laden. Indeed, as FIG. 2 shows, the top-10 pages returned by a Google query "Saudi magnate half-brother" are all related to the Bin Laden family. There is currently no way to detect this inference, as well as potentially many others. It is important to anticipate and counter such undesired inferences in a thorough redaction process.

A system that detects such undesired inferences can benefit a wide range of industries. In the legal service industry, for example, documents protected by attorney-client privilege are generally redacted to protect parties' private information. In the healthcare industry, it is common practice, and sometimes mandated by the law, to redact sensitive information, such as HIV status, drug or alcohol abuse, and mental health conditions, from medical records prior to releasing them. Among individuals, anonymous bloggers are a good example of people who value anonymity. However, remaining anonymous can be challenging, because a small amount of personal information may suffice to infer one's identity with the help of powerful search engines.

In all these instances, the challenge is not only access control, but also inference control. Assuming that a mechanism exists to control access to a subset of information, the problem is to determine what information can be released publicly without compromising certain secrets. That is, which portion of the information can be disclosed. What makes this problem difficult is the quantity and complexity of inferences that arise when published data is combined with, and interpreted against, the backdrop of public knowledge and outside data.

Embodiments of the present invention provide a system for inference detection. This system operates not only in a restricted setting, for example with database tables or other forms of structured data, but also in all its generality with unstructured data. The underlying operation principle is that the Web, or any pool of knowledge, works equally well for generating inferences and detecting inferences.

In one embodiment, the system first extracts salient keywords from the private data intended for release. Then, the system issues search queries for documents that match subsets of these keywords, within a reference corpus (such as the public Web) that encapsulates as much of relevant public knowledge as possible. The system subsequently parses the documents returned by the search queries and identifies keywords not present in the original to-be-released data. These additional keywords facilitate an estimation of the likelihood of certain inferences. The system then flags potentially dangerous inferences for manual review.

In this disclosure, "corpus" refers to a collection of documents. In one embodiment, the corpus can include all the documents available on the Web. Additionally, the system can operate based on one or more corpora. "Documents" are understood here to be any form of content, including textual documents, spreadsheets, presentations, images, video, audio, multimedia, presentations, and so forth. Furthermore, a document can be paper-based or electronic.

Web-Based Inference Detection

The following description presents an exemplary operation model of a Web-based inference detection tool. This model is not restrictive and is only for illustration purposes. Furthermore, there can be various ways to implement this model. For example, embodiments of the present invention can be implemented in a computer system, or over a collection of networked computers, such as a server farm, a cluster of computers, or a distributed computing collaboration. Different embodiments can also be implemented in hardware and/or software. A mathematical description of the operation model is presented as follows.

Let C denote a private collection of documents considered for public release, and let R denote a corpus or a collection of corpora. Note that a corpus is a collection of reference documents. For example, collection C can include the blog entries of a writer, and collection R can include all the documents publicly available on the Web.

Let K(C) denote all the knowledge that can be computed from private collection C. The set K(C) represents all the statements and facts that can be derived from the information contained in collection C. Theoretically, the set K(C) can be computed with a complete and sound theorem prover given all the axioms in C. In practice, however, the costs for such computation can be prohibitively high. Therefore, one embodiment of the present invention uses an approximate representation of K(C). Similarly, let K(R) denote all the knowledge that can be computed from the reference collection R.

Undesired inferences can arise when the knowledge that can be extracted from the union of the private and reference collections, K(C∪R), is greater than the union of the knowledge that can be extracted separately from C and R, K(C)∪K(R). The inference control problem is therefore the problem of controlling the difference $$\delta(C,R)=K(C\cup R)-\{K(C)\cup K(R)\}.$$

For example, assume that the collection C includes the declassified document as is illustrated in FIG. 1, and that R includes all the information publicly available on the Web. Let S denote the statement: "The declassified FBI document is a biography of Osama Bin Laden." Since the identity of the person to whom the document pertains has been redacted, it is very difficult, if not impossible, to derive statement S from C alone. Therefore, S∉K(C). The statement S is clearly not in K(R) either, since one cannot derive from R alone a statement about a document that is in C but not in R. Hence, S does not belong to K(C)∪K(R). However, as shown earlier, the statement S belongs to K(C∪R). That is, one can learn from C that the document pertains to an individual characterized by the keywords "Saudi," "magnate," "half-brothers," "Yemen," etc. Furthermore, one can learn from R that these keywords are closely associated with "Osama Bin Laden." As illustrated above, by combining these two sources of information, one can learn that the statement S is true with a high probability.

It is critical to a publisher to understand δ(C,R) prior to publishing the collection C of private documents, to ensure that the publication of C does not allow for unwanted inferences. The owner of C may choose to withhold from publication parts or all of the documents in the collection based on an assessment of the difference δ(C,R). Sometimes, a set of sensitive knowledge that should not be leaked, denoted as K*, is explicitly specified. In this case, the inference control problem becomes the problem of ensuring that the intersection δ(C,R)∩K* is empty.

Basic Approach

In the description herein, private collection C can contain an arbitrary collection of documents. In particular, these documents are not restricted to structured data, such as XML-based documents. Furthermore, collection R is assumed to contain all publicly available documents. In one embodiment, R contains all the information publicly available on the Web. In general, a system that facilitates inference detection performs the following two operations. First, the system learns the content of the documents in private collection C. Next, the system determines the inferences that can be drawn from the combination of C and R.

In one embodiment, to derive knowledge from documents in C, the system employs automated content analysis to extract keywords in these documents. The system can use any natural language processing (NLP) tool, ranging from text extraction to in-depth linguistic analysis. In one embodiment, the system selects keywords based on a "term frequency-inverse document frequency" (TF.IDF) analysis. Note that the term "keyword" as used in this disclosure is not limited to a single word, but can include words, phrases, abbreviations, synonyms, or any combination of language symbols.

In a TF.IDF analysis, the system assigns each word in a document a TF.IDF weight. The system uses this weight, which is a statistical measure, to evaluate how important a word is to a document in a corpus. The importance of a word increases proportionally to the number of times the word appears in the document, but is offset by the frequency of the word occurrence in the corpus. For example, the TF.IDF weight of a term i, denoted as $t_i$, with regard to a given document can be computed as follows:

$$W_{TF.IDF} = \frac{n_i}{\sum_k n_k} \cdot \log\frac{|D|}{|\{d:t_i \in d\}|}.$$

In this formula, term frequency $$\frac{n_i}{\sum_k n_k}$$

is the number of occurrences of $t_i$ in the document, normalized by all the term occurrences in the document. The inverse document frequency, $$\log\frac{|D|}{|\{d:t_i \in d\}|},$$

is a measure of the general importance of the term and is computed as the logarithm of the number of all documents in the corpus divided by the number of documents containing the term $t_i$.

The above formula for computing TF.IDF weight is only one example of TF.IDF definition. For different applications, different TF.IDF definitions can be adopted. In addition, embodiments of the present invention can also use other linguistic analysis approaches to derive knowledge from a document.

Next, to determine inferences that can be drawn from the combination of C and R, the system issues search queries for documents that match subsets of the keywords previously extracted. The system issues these queries within a reference corpus, such as the public Web, that encapsulates as much of relevant public knowledge as possible. The system then parses the documents returned by the search queries for keywords not present in the original private document. Based on these additional keywords, the system can automatically estimate the likelihood of certain inferences. In one embodiment, potentially dangerous inferences are flagged for manual review.

FIG. 3 presents an exemplary block diagram illustrating the process of Web-based inference detection in accordance with an embodiment of the present invention. The system first receives a set of private documents 302, which constitute the private collection C, and applies an NLP analysis 304 to private documents 302. In response, the system obtains a set of knowledge representation 306 for private documents 302. In one embodiment, knowledge representation 306 includes a number of keywords.

Based on knowledge representation 306, the system formulates a number of queries 310, and issues these queries to a search engine 312. Search engine 312 conducts the corresponding searches on a set of reference documents (corpus) 308. Note that although in one embodiment corpus 308 includes all the public information on the Web, corpus 308 can also include other format of media. For example, corpus 308 can be all the public court documents, medical records, or all the books in a library.

Search engine 312 then returns a number of hits 314. The system performs hit analysis 316 and compares the analysis result with a set of sensitive information 368. As a result, the system derives inferences 320, which can be used to redact private documents 302.

Inference Detection

The inference-detection system described herein illustrates only one embodiment of the present invention. A wide range of NLP tools can be incorporated into the general inference-detection model and achieve the same, if not better, results. The following section describes the inputs, outputs, and parameters of a generic inference-detection model.

Inputs: A private collection of documents $C=\{C_1, \ldots, C_n\}$, a collection of reference documents R, and a list of sensitive keywords K* that represents sensitive knowledge.

Output: A list L of inferences that can be drawn from the union of C and R. Each inference is of the form $(C_{i1}, \ldots, C_{ik})$ $W^*$, wherein $(C_{i1}, \ldots, C_{ik}) \subseteq C$ is a subset of documents in C, and $W^* \subseteq K^*$ is a subset of sensitive keywords. The inference $(C_{i1}, \ldots, C_{ik}) \Rightarrow W^*$ indicates that the documents $(C_{i1}, \ldots, C_{ik})$, together with the knowledge present in R, allow for inference of the sensitive keywords $W^*$. Note that the output of the system can be a mapping relationship between one or more documents to a piece of sensitive knowledge. The system returns an empty list if it fails to detect any sensitive inference.

Parameters: This inference-detection model is parameterized by four parameters. Parameter $\alpha$ controls the depth of the NLP analysis of the documents in C. Parameters $\beta$ and $\gamma$ control the search depth for documents in R that are related to C. Parameter $\delta$ controls the depth of the NLP analysis of the documents retrieved by the search engine. In one embodiment, the values of $\alpha$, $\beta$, $\gamma$, and $\delta$ are all positive integers. These parameters can be tuned to achieve different trade-offs between the running time of the model and the completeness and quality of inference detection.

The system implements and executes the inference-detection model in the following two stages.

Understanding the documents in C. The system performs a TF.IDF analysis to extract from each document $C_i$ in the collection C the top $\alpha$ keywords that are most representative of $C_i$. Let $S_i$ denote the set of the top $\alpha$ keywords extracted from document $C_i$.

Inference detection. The list L of inferences is initially empty. The system considers in turn every subset $C' \subseteq C$ of size $|C'| \leqq \beta$. For every such subset $C' = (C_{i1}, \ldots, C_{ik})$, with $k \leqq \beta$, the system performs the following operations. For every vector of keywords $(W_{i1}, \ldots, W_{ik})$ in the Cartesian product $S_{i1} \times \ldots \times S_{ik}$:

1. The system uses a search engine to retrieve from the collection R of reference documents the top $\gamma$ documents that contain all the keywords $(W_{i1}, \ldots, W_{ik})$.
2. With the TF.IDF analysis, the system extracts the top $\delta$ keywords from this collection of $\gamma$ documents. In one embodiment, these keywords are extracted from the aggregate collection of $\gamma$ documents as if all these documents were concatenated into a single large document, not from each individual document.
3. Let $W^*$ denote the intersection of the $\delta$ keywords obtained from operation 2 with the set $K^*$ of sensitive keywords. If $W^*$ is non-empty, the system adds inference $C' \Rightarrow W^*$ to L. The system then outputs the list L and exits.

The system can further use additional queries to gauge, or rank, the strength of the inference between an identified suspicious keyword in the original document and a sensitive keyword, after obtaining the list L. In one embodiment, the system computes a sensitive-hits ratio, which in one embodiment is defined as the number of the search hits from a query containing both the suspicious keyword and the sensitive keyword, to the number of search hits from a query containing only the suspicious keyword. The system then ranks the keywords in the original documents according to the strength or severity of their inferences. For example, to evaluate the likelihood that a patient taking the drug naltrexone is alcoholic, the system can issue a first query for "naltrexone," retrieving x documents, and a second query for "naltrexone alcoholism," retrieving y documents. The system can then calculate the ratio y/x. If this ratio is fairly close to 1, one might decide that naltrexone should be removed from all medical records to avoid inferring a patient's alcoholism condition.

Note that the system can also use the aforementioned sensitive-hits ratio computation method as the main approach, instead of an add-on, to identify inferences. In one embodiment, the system first extracts the keywords from a set of given private documents using NLP tools. For each keyword extracted from the private documents, the system then computes the sensitive-hits ratio for each extracted keyword with respect to each sensitive word or phrase. If the sensitive-hits ratio between a keyword and a sensitive word or phrase is greater than a given threshold, the system identifies an inference between this keyword and the sensitive word or phrase. Furthermore, the system can also receive a set of sensitive words or phrases and the extracted keyword can include one or more multi-word phrases. For example, the system can extract three phrases, "blood shot eyes," "memory loss," and "liver disease," and compute a sensitive-hits ratio for sensitive words associated with alcoholism, such as "alcoholism," "alcohol," "alcoholic," "drunk," "drinking." To compute the sensitive-hits ratio, the system first issues a query for "blood shot eyes memory loss liver disease," and then a query for "blood shot eyes memory loss liver disease AND (alcoholism OR alcohol OR alcoholic OR drunk OR drinking)." The system then computes the ratio between the number of hits returned by the second query to the number of hits returned by the first query. In general, the system can combine any number of extracted words or phrases in generating the queries.

Variations

The aforementioned inference-detection model can be tailored to a variety of applications.

In some embodiments, the system can employ any given logic relationship when formulating queries based on a number of keywords. Although the examples described herein are based on queries containing space-separated keywords, the system can adopt any Boolean-formulated queries. For example the system can insert "AND" or "OR" between the keywords. With some advanced search engines, the system can also specify how the keywords should appear in the document, such as within a certain number of paragraphs, sentences, or words. Furthermore, the system can also analyze the keywords and formulating the queries based on the analysis. For example, if the system determines that two keywords are synonyms or closely related, the system can optionally insert an "OR" between the keywords when formulating a query.

In further embodiments, the system can intelligently select different corpora according to the documents under test. The system can also select corpora based on the intended audience.

In some embodiments, the set of sensitive knowledge $K^*$ may not be known or may not be specified. Therefore, the system identifies all possible inferences that arise from knowledge of the collection of documents C and the reference collection R. A variation of the inference-detection model handles this case. In operation 3 of the inference-detection stage, the system records all inferences instead of only inferences that involve keywords in $K^*$. Note that this is equivalent to assuming that the set $K^*$ of sensitive knowledge includes all knowledge. The system may also track the number of occurrences of each inference, so that the list L can be sorted from the most to the least frequent inference.

The aforementioned model assumes that the sensitive knowledge $K^*$ is given as a set of keywords. Other representations of sensitive knowledge are also possible. In one embodiment, sensitive knowledge may be based on a topic, such as alcoholism or sexually transmitted diseases, instead of a list of keywords. To handle this case, the system performs a pre-processing operation which converts a sensitive topic into a list of sensitive keywords. One way of doing so is to issue a search query for documents in the reference collection R that contain the sensitive topic, and use TF.IDF analysis to extract from these documents an expanded set of sensitive keywords for the sensitive topic.

Figure 4:
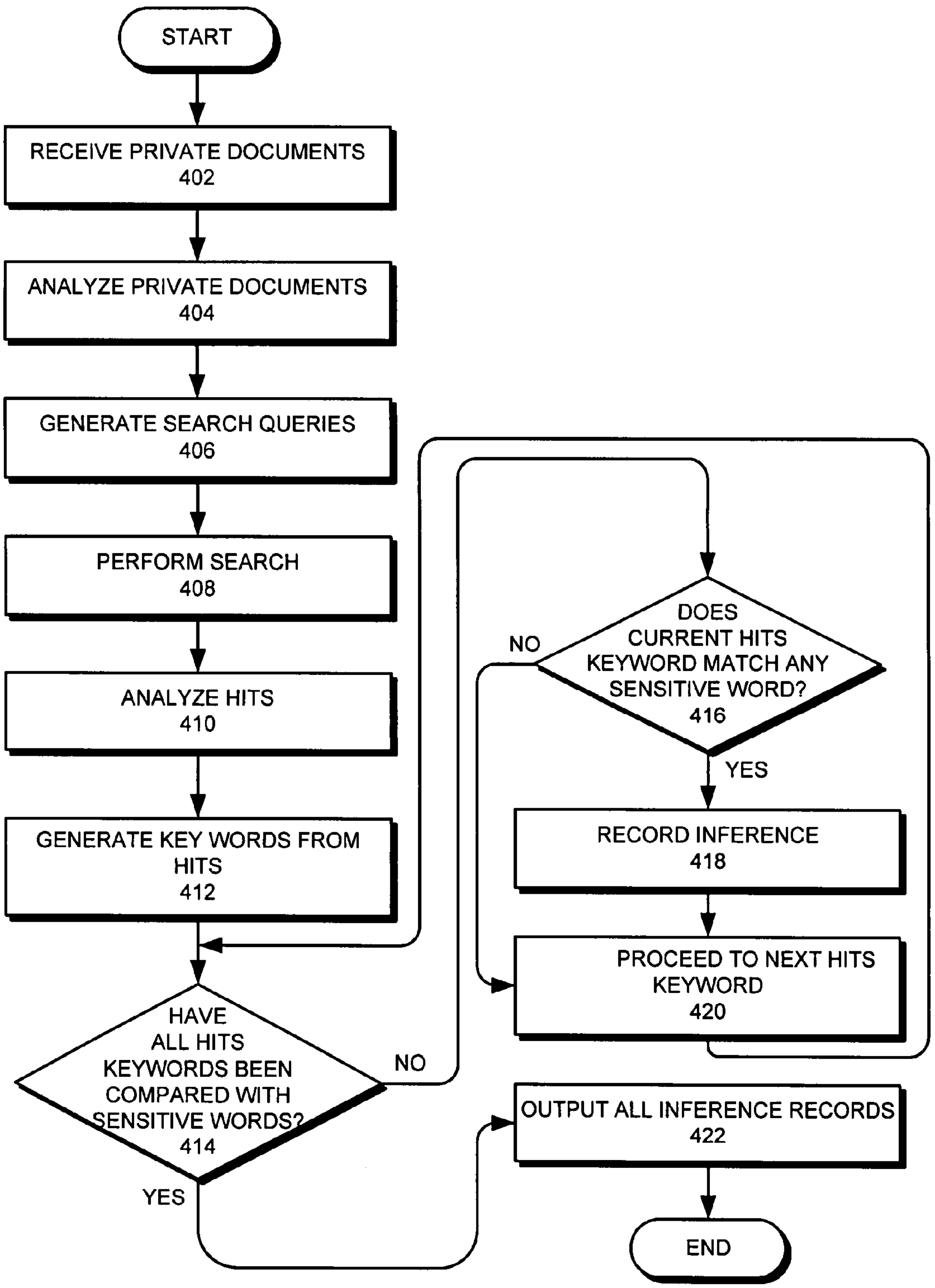
FIG. 4 presents an exemplary flow chart illustrating the process of Web-based inference detection in accordance with an embodiment of the present invention.

FIG. 4 presents an exemplary flow chart illustrating the process of Web-based inference detection in accordance with an embodiment of the present invention. During operation, the system receives a set of private documents (operation 402). The system analyzes these private documents (operation 404) and generates the corresponding search queries (operation 406). A search engine then performs searches on the Web based on these queries and returns a number of hits (operation 408).

Subsequently, the system analyzes the hits returned by the search engine (operation 410) and generates keywords from these hits (operation 412). The system then determines whether all hits keywords have been compared with the sensitive words (operation 414). If so, the system outputs the inference records (operation 422) and exits. Otherwise, the system further determines whether the current hits keyword matches any sensitive word (operation 416). If there is a match, the system records the inference (operation 418), and proceeds to the next hits keyword (operation 420). If there is not a match, the system proceeds to the next hits keyword (operation 420).

Figure 5:
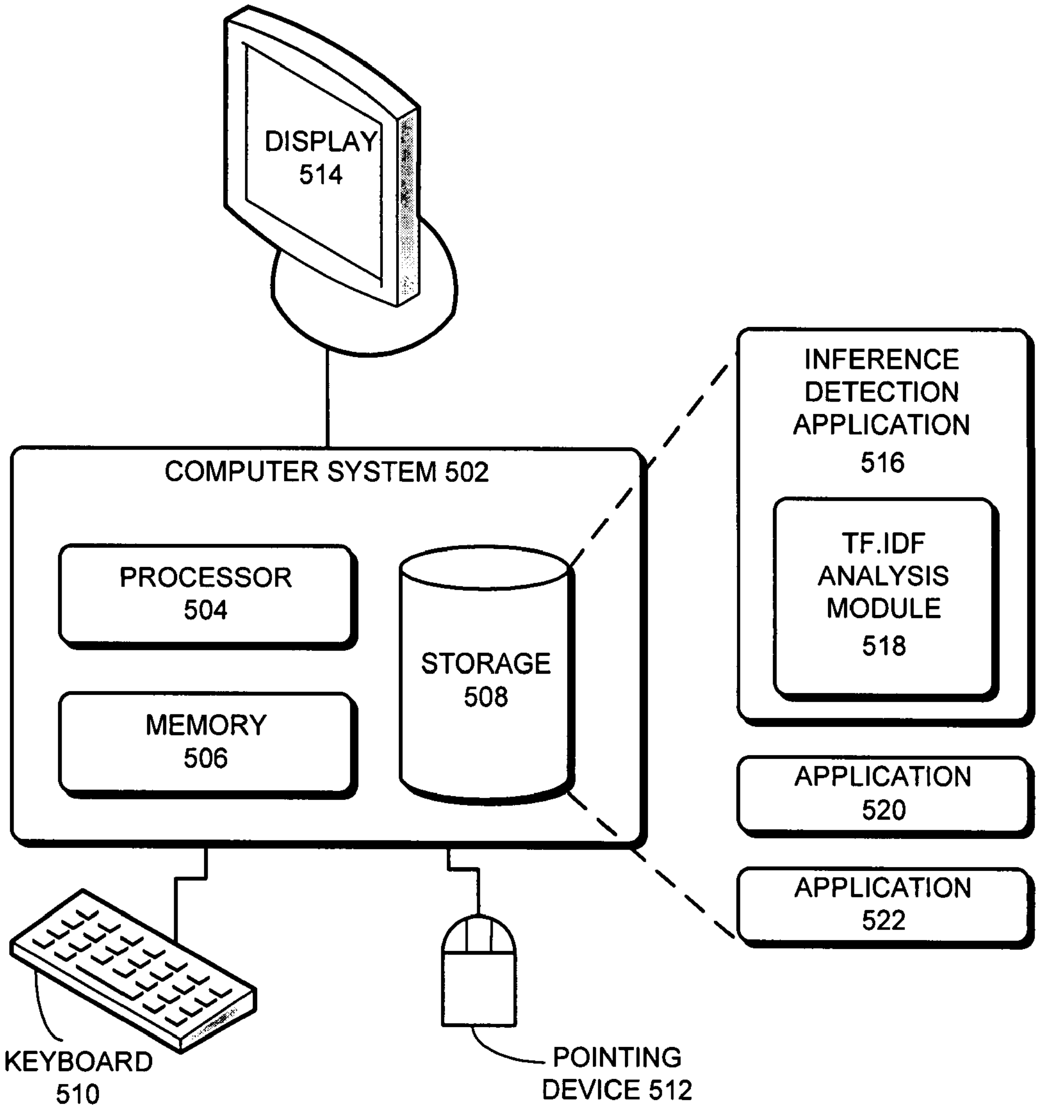
FIG. 5 illustrates a computer system for facilitating Web-based inference detection in accordance with one embodiment of the present invention.

FIG. 5 illustrates a computer system for facilitating Web-based inference detection in accordance with one embodiment of the present invention. A computer system 502 includes a processor 504, a memory 506, and a storage device 508. Computer system 502 is also coupled to a display 514, a keyboard 510, and a pointing device 512. Storage device 508 stores an inference detection application 516, and applications 520 and 522. In addition, inference detection application 516 contains a TF.IDF analysis module 518, which performs keyword extraction from documents during inference detection. During operation, inference detection application 516 is loaded into memory 506 and executed by processor 504. Note that computer system 502 can be coupled to the Internet, whereby the Web searches are performed by a separate search engine.

Exemplary Applications

This section describes a wide array of potential applications for Web-based inference detection.

Redaction of medical records. Medical records are often released to third parties such as insurance companies, research institutions or legal counsel in the case of malpractice lawsuits. State and federal legislation mandates the redaction of sensitive information from medical records prior to release. For example, all references to drugs or alcohol, mental health, and HIV status are typically redacted. This redaction task is far more complex than it may initially appear. Extensive and up-to-date knowledge of diseases and drugs is usually required to detect all clues and combinations of clues that may allow for inference of sensitive information. Since this medical information is readily available on public websites, the process of redacting sensitive information from medical records can be partially automated with Web-based inference control.

Preserving individual anonymity. Intelligence and other governmental agencies are often required by law (such as the Freedom of Information Act) to release publicly documents that pertain to a particular individual or group of individuals. To protect the privacy of those concerned, the documents are released in a form that does not allow for unique identification. This problem is notoriously difficult, because seemingly innocuous information may allow for unique identification. In the previously illustrated example, the FBI published a poorly redacted biography of Osama Bin Laden. Directly identifying information, such as first and last names, is correctly expunged from the biography. However, the biography still contained keywords such as "half-siblings," "Saudi," "magnate," and "Yemen," which apply to very few individuals and gave away Bin Laden's identity. Web-based inference control is perfectly suited to the detection of indirect inferences based on publicly available data. This tools can be used to determine how much information can be released about a person, entity, or event while preserving k-anonymity, that is, ensuring that the sensitive information remains hidden in a group of like-entities of size at least k, and cannot be identified any more precisely within the group.

Formulation of redaction rules. The Web-based inference-detection tools can also be used to pre-compute a set of redaction rules that is later applied to a collection of private documents. For a large collection of private documents, pre-computing redaction rules may be more efficient than using Web-based inference detection to analyze each and every document. In 1995, for example, executive order 12958 mandated the declassification of large amounts of government data, which include hundreds of millions of pages. Sensitive portions of documents were to be redacted prior to declassification. The redaction rules are exceedingly complex and formulating them is reportedly nearly as time-consuming as applying them. Web-based inference detection is an appealing approach to automatically expand a small set of seed redaction rules. For example, assuming that the keyword "missile" is sensitive, web-based inference detection could automatically retrieve other keywords related to missiles, e.g. "guidance system," "ballistics," and "solid fuel," and add them to the redaction rule.

Public image control. This application considers the problem of verifying that a document conforms to the intentions of its author, and does not accidentally reveal private information or information that could easily be misinterpreted or understood in the wrong context. This application does not assume that the set of unwanted inferences is known or explicitly defined. Instead, the goal of this application is to design a broad, general-purpose tool that helps contextualize information and may draw an author's attention to a broad array of potentially unwanted inferences. For example, Web-based inference detection could alert the author of a blog to the fact that a particular posting contains a combination of keywords that will make the blog appear prominently in the results of some search query.

Leak detection. This application helps a data owner avoid accidental releases of information that was not previously public. In this application, the set of sensitive knowledge K* includes all information that was not previously public. In other words, the release of private data should not add anything to public knowledge.

Experiments

This section presents several experiments that focus on exploring two Web-based inference-detection applications, namely preserving individual anonymity and redaction of medical records.

Ideally, Web-based inference detection is applied to authentic documents for which privacy is a chief concern. For example, a corpus of medical records being prepared for release in response to a subpoena would be ideal for evaluating the ability of these techniques to identify sensitive topics. However, such a corpus is difficult to obtain. Similarly, a collection of anonymous blogs would be ideal for testing the ability of these techniques to identify individuals, but such blogs are difficult to locate efficiently.

Given the difficulties of finding unequivocally sensitive data on which to test the inference-detection model, the system uses instead publicly available information about an individual, which is anonymized by removing the individual's first and last names. In most cases, the public information about the individual, thus anonymized, appears to be a decent substitute for text that the individual might have authored on their blog or Web page.

In one embodiment, the system employs Java for extracting text from html, calculation of an extended form of TF.IDF for identifying keywords in documents, and the Google SOAP search API for making Web queries based on those keywords.

The exemplary code used herein removes html tags for extracting text from html. In the following experiments, the system performs repeated extractions from similarly formatted html pages, such as Wikipedia biographies.

In one embodiment, the TF.IDF "rank" of a word in a document is defined with respect to a corpus, C. Note that the TF.IDF definition here is slightly different from the one provided previously, thus demonstrating the flexibility in the inference-detection model in terms of adopting different computation methods. The definition is provided as follows.

Definition 1 Let D be a document that contains the word Wand is part of the corpus of documents, C. The term frequency (TF) of W with respect to D is the number of times W occurs in D. The document frequency (DF) of W with respect to the corpus, C, is the total number of documents in C that contain the keyword W. The TF.IDF value associated with W is the ratio: TF/DF.

In one embodiment, the system implements a variant of TF.IDF in which the system first uses the British National Corpus (BNC) to stem lexical tokens. For example, the tokens "accuse," "accused," "accuses," and "accusing" would be mapped to the stem "accuse." The system then uses the BNC again to associate with each token the DF of the corresponding stem, e.g., "accuse" in the earlier example.

Web-Based De-Anonymization.

In this experiment, the goal is to demonstrate how keyword extraction can be used to warn the end-user of impending identification. In one embodiment, the inventive inference-detection system accomplishes this goal by constantly amassing keywords from online content proposed for posting by the user (e.g. blog entries) and issuing Web queries based on those keywords. The user is alerted when the hits returned by those queries return their name, and thus is warned about the risk of posting the content.

This experiment is based on Wikipedia biographies standing in for user-authored content. The biography subject's name is removed from the biography. The personal content in the biography is viewed as a condensed version of the information an individual might reveal over many posts to their blog, for example. From these "anonymized" biographies, the system extracts keywords and forms queries to Google based on subsets of these keywords.

The system then searches a portion of the returned hits for the biography subject's name and raises a flag when a hit that is not a Wikipedia page mentions the biography subject. For efficiency reasons, the system limits the portion and number of Web pages to be examined. In particular, the experiment includes the following operations:

Input: Wikipedia biography, B:

1. Extract the subject, N, of the biography, B, and parse N into a first name, $N_1$ optional middle name or middle initial, $N_1'$, and a last name, $N_2$ (where $N_j$ is empty if a name in that position is not given in the biography).
2. Extract the top 20 keywords from a Wikipedia biography, B, forming the set, $S_B$, through the following steps:

(a) Extract the text from the HTML file.

(b) Calculate the enhanced TF.IDF ranking of each word in the extracted text. If present, remove $N_1$, $N_1'$ and $N_2$ from this list, and select the top twenty words from the remaining text as the ordered set, $S_B$.

3. For x=20, 19, . . . , 1, issue a search-engine query on the top x keywords in $S_B$. Denote this query as $Q_x$. For example, if $W_1$, $W_2$, $W_3$ are the top 3 keywords, the search query $Q_3$ is: $W_1$ $W_2$ $W_3$, with no additional punctuation. Let $H_x$ denote the set of hits returned by the search engine with the restrictions that the hits contain only html or text files and that no hits from en.wikipedia.org be returned.
4. Let $H_{x,1}, H_{x,2}, H_{x,3} \in H_x$ be the first, second, and third hits, respectively, resulting from query $Q_x$. For x=20, 19, . . . , 1, determine if $H_{x,1}$, $H_{x,2}$, and $H_{x,3}$ contain references to subject N by searching for contiguous occurrences of $N_1$, $N_1'$, and $N_2$ within the first 5000 lines of html code in each of $H_{x,1}$, $H_{x,2}$, and $H_{x,3}$. Record any such occurrences.

Output: $S_B$, each query $Q_x$ that contains $N_1$, $N_1'$, and $N_2$ contiguously in at least one of the three examined hits, and the URL of the particular hit(s).

Figure 6:
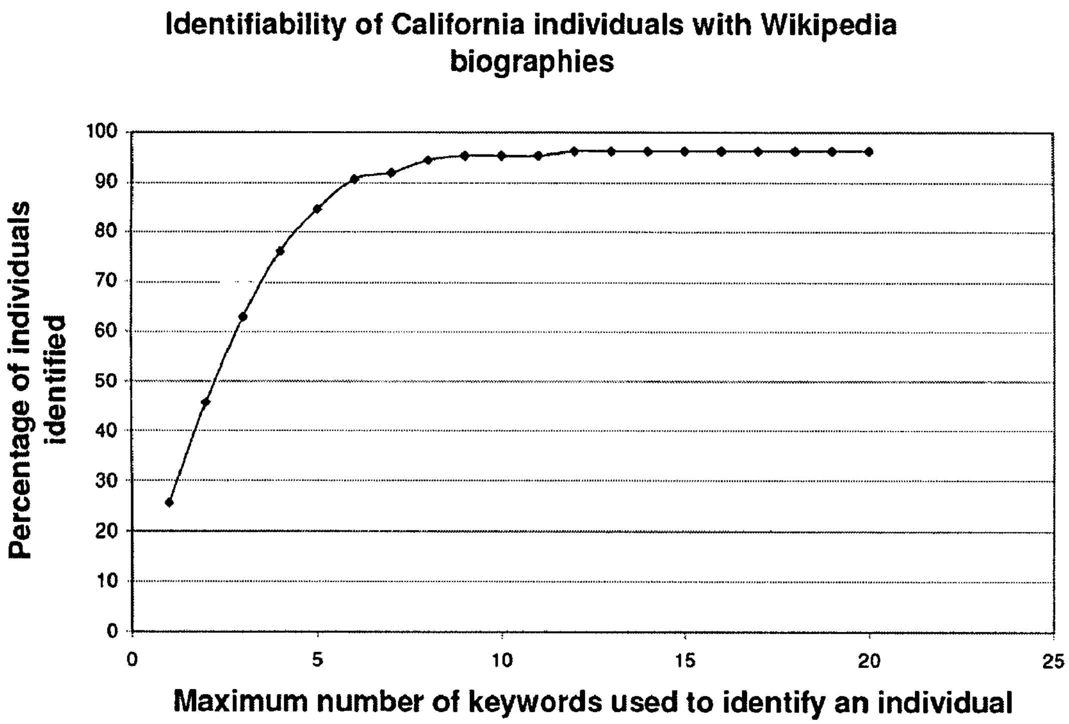
FIG. 6 illustrates a set of inference-detection results for identifying individuals in California in accordance with one embodiment of the present invention.
Figure 7:
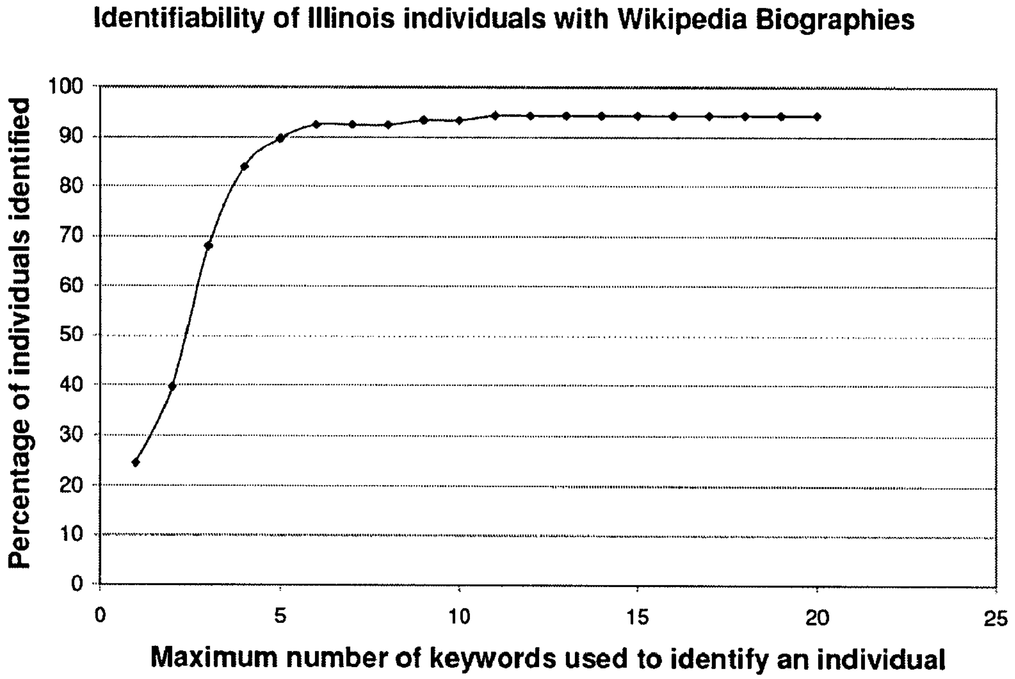
FIG. 7 illustrates a set of inference-detection results for identifying individuals in Illinois in accordance with one embodiment of the present invention.

In this experiment, the system performs an inference-detection test on 234 biographies of California residents and 106 biographies of Illinois residents contained in Wikipedia. The results for both states are shown in FIGS. 6 and 7, and are very similar. In each case, 10 or fewer keywords extracted from the Wikipedia biography suffice to identify almost all the individuals. Note that the statistics shown in FIGS. 6 and 7 are based solely on the machine output, with no human review.

TABLE 1

| Keywords | URL of Top Hit | Name of Person |
|---|---|---|
| campaigned soviets | http://www.utexas.edu/features/archive/2004/election policy.html | Ronald Reagan |
| defense contra reagan | http://www.pbs.org/wgbh/amex/reagan/peopleevents/pande08.html | Caspar Weinberger |
| reagan attorney edit pornography | http://www.sourcewatch.org/index.php?title=Edwin Meese III | Edwin Meese |
| nfl nicole goldman francisco pro | http://www.brainyhistory.com/years/1997.html | O. J. Simpson |
| kung fu actors | http://www.amazon.com/Kung-Fu-Complete-Second-Season/dp/B0006BAWYM | David Carradine |
| medals medal raid honor aviation | http:/www.voicenet.com/~lpadilla/pearl.html | Jimmy Doolittle |
| fables chicago indiana | http://www.indianahistory.org/pop hist/people/ade.html | George Ade |
| wisconsin illinois chicago architect designed | http://www.greatbuildings.com/architects/Frank Lloyd Wright.html | Frank Lloyd Wright |

TABLE 1 presents example inferences between keywords, URLs, and biography subjects. These results illustrate that the associations a person has may be as useful for identifying them as their personal attributes. For example, 50% of the first page of hits returned from the search query "nfl nicole goldman francisco pro" are about O. J. Simpson (including the top three hits), but there is no reference to O. J. Simpson in any of the first page of hits returned by the query "nfl francisco pro." Hence, the association of O. J. Simpson with his wife (Nicole) and his wife's boyfriend (Goldman) is very useful to identifying him in the pool of professional football players who once were members of the San Francisco 49ers.

Web-Based Sensitive Topic Detection.

Another application of Web-based inference detection is redaction of medical records. It is common practice to redact all information about diseases such as HIV/Aids, mental illness, and drug and alcohol abuse, prior to releasing medical records to a third party, such as a judge in medical malpractice litigation. Implementing such protections today relies on the thoroughness of the redaction practitioner to keep abreast of all the medications, physician names, diagnoses, and symptoms that might be associated with such conditions and practices. Web-based inference detection can be used to improve the thoroughness of this task by automating the process of identifying the keywords allowing such conditions to be inferred.

In one embodiment, the system takes as input an authoritative page about a certain disease. In this experiment, the system uses Wikipedia to supply pages for alcoholism and sexually transmitted diseases (STDs). The system then extracts the text from the html, and identifies the keywords. To identify keywords that might allow the associated disease to be inferred, the system issues search queries on subsets of keywords and examines the top hits for references to the associated disease. If such a reference is found, the system records those keywords as being potentially inference-enabling. In practice, a redaction practitioner may then use this output to decide what words to redact from the medical records before releasing them to preserve the privacy of the patient. The following describes this experiment in more detail.

Input: An ordered set of sensitive words, $K^*=\{v_1, \ldots, v_b\}$, for some positive integer b, and a page, B. B is either the Wikipedia page for alcoholism, STDs, or a "control" page of general medical terms.

1. If B is a Wikipedia page, extract the top 30 keywords from B, forming the set $S_B$, through the following steps:
(a) Extract the text from html.
(b) Calculate the enhanced TF.IDF ranking of each word in the extracted text. Select the top 30 words as the ordered set, $S_B=\{W_1, W_2, \ldots, W_{30}\}$.
2. If B is a medical terms page, extract the terms using code customized for that Web site and let $W_B=\{W_1, W_2, \ldots, W_{30}\}$ be a subset of 30 terms from that list, where the selection method varies with each run of the experiment.
3. For each pair of words $\{W_i, W_j\} \in S_B$, let $Q_{i,j}$ be the query containing those two words with no additional punctuation and the restriction that no pages from the domain of source page B be returned, and that all returned pages be text or html (to avoid parsing difficulties). Let $H_{i,j}$ denote the first hit returned after issuing query $Q_{i,j}$ to search, after known medical terms Web sites are removed from the search results.
4. For all $i,j \in \{1, \ldots, 30\}$, $i \neq j$, and for $l \neq \{1, \ldots, b\}$, search for the string $v_l \in K^*$ in the first 5000 lines of $H_{i,j}$. If $v_l$ is found, record $v_l$, $w_i$, $w_j$ and $H_{i,j}$ and discontinue the search.

Output: All triples ($v_l$, $Q_{i,j}$, $H_{i,j}$) found in operation 3.

RESULTS FOR STD EXPERIMENTS. In one embodiment, the system performs the above inference detection on a Wikipedia page about STDs, B, and a selected set, B', of 30 keywords from the medical term index available at http://www.medterms.com/script/main.hp.asp. The set B' was selected by starting at the 49th entry in the medical term index and selecting every 400th word in order to approximate a random selection of medical terms. Keyword pairs from input B generate far more hits for STDs (306/435>70%) than keyword pairs from B' (108/435<25%). The results are summarized in FIG. 9.

RESULTS FOR ALCOHOLISM EXPERIMENTS. In one embodiment, the system performs the above inference detection on a Wikipedia page about alcoholism, B, and a selected set, B', of 30 keywords from the medical term index available at http://www.medterms.com/script/main.hp.asp. For the run analyzed in FIG. 9, the set B' was selected by starting at the 52nd entry in the medical term index and selecting every 100th word until 30 were accumulated in order to approximate a random selection of medical terms. Keyword pairs from input B are observed to generate far more hits for alcoholism (47.82%) than B (9.43%). In addition, manual review was performed on the URLs that yielded a hit in $v \in K^*$ for a seemingly innocuous pair of keywords. These results are summarized in FIG. 9.

Note that, although the aforementioned examples illustrate detection of undesired inferences, embodiments of the present invention can readily be used to detect desired or neutral inferences for a wide range of purposes. In addition, the foregoing descriptions of embodiments of the present invention have been presented only for purposes of illustration and description. They are not intended to be exhaustive or to limit the present invention to the forms disclosed. Accordingly, many modifications and variations will be apparent to practitioners skilled in the art. Additionally, the above disclosure is not intended to limit the present invention. The scope of the present invention is defined by the appended claims.

What is claimed is:

1. A computer-implemented method for detecting inferences from documents, wherein the computer includes a processor, the method comprising:
receiving one or more documents;
extracting a first set of knowledge relevant to the documents;
formulating one or more queries to one or more reference corpora based on the first set of knowledge;
extracting a second set of knowledge from results received in response to the queries; and
detecting an inference by producing a mapping relationship between at least one document and a piece of the second set of knowledge which is not within the first set of knowledge, wherein the mapping relationship indicates an inference from the documents.

2. The method of claim 1, wherein extracting the first set of knowledge relevant to the document comprises deriving a set of words or phrases relevant to each document.

3. The method of claim 2, wherein deriving the set of words or phrases further comprises determining a term-frequency inverse-document-frequency (TF.IDF) weight for a word or phrase contained in the document.

4. The method of claim 1, wherein extracting the first set of knowledge comprises extracting a set of words or phrases from each document; and
wherein formulating the queries comprises constructing single-word queries, multi-word queries, or both from the extracted words or phrases.

5. The method of claim 4, wherein constructing the queries further comprises applying one or more pre-determined logical combinations of the extracted words or phrases.

6. The method of claim 4, wherein extracting a set of words or phrases from each document comprises extracting a pre-determined number of words or phrases from the document.

7. The method of claim 1, further comprising retrieving a pre-determined number of results for each query.

8. The method of claim 1, further comprising receiving a set of sensitive knowledge relevant to the documents;

wherein the piece of the second set of knowledge mapped to the document is also within the set of sensitive knowledge; and wherein producing the mapping relationship comprises determining an intersection between the set of sensitive knowledge and the second set of knowledge.

9. The method of claim 1, wherein producing the mapping relationship comprises presenting one or more words or phrases from the documents, which words or phrases correspond to the first set of knowledge, and one or more sensitive words or phrases extracted from the query results.

10. The method of claim 1, further comprising:

determining a ratio of:

the number of results returned by a first query based on one or more words or phrases from the documents and one or more sensitive words or phrases, to the number of results returned by a second query based on one or more words or phrases from the documents; and determining an inference from the one or more words or phrases used to generate the first query based on the size of the ratio.

11. The method of claim 1, further comprising:

selecting the one or more reference corpora based on the documents, an intended audience, or both.

12. The method of claim 1, further comprising:

detecting one or more undesired inferences, wherein the undesired inferences are information intended to remain private, which can be extracted from a union of the document and the corpus and which cannot be extracted from the document or the corpus alone.

13. A computer system for detecting inferences from documents, the computer system comprising:

a processor;

a memory;

a receiving mechanism configured to receive one or more documents;

a first knowledge extraction mechanism configured to extract a first set of knowledge relevant to the documents;

a query formulation mechanism configured to formulate one or more queries to one or more reference corpora based on the first set of knowledge;

a second knowledge extraction mechanism configured to extract a second set of knowledge from results received in response to the queries; and a detecting mechanism configured to detect an inference by producing a mapping mechanism configured to produce a mapping relationship between at least one document and a piece of the second set of knowledge which is not within the first set of knowledge, wherein the mapping relationship indicates an inference from the documents.

14. The computer system of claim 13, wherein while extracting the first set of knowledge relevant to the document, the first knowledge extraction mechanism is configured to derive a set of words or phrases relevant to each document.

15. The computer system of claim 14, wherein while deriving the set of words or phrases, the first knowledge extraction mechanism is further configured to determine a term-frequency inverse-document-frequency (TF.IDF) weight for a word or phrase contained in the document.

16. The computer system of claim 13, wherein while extracting the first set of knowledge, the first knowledge extraction mechanism is configured to extract a set of words or phrases from each document; and wherein while formulating the queries, the query formulation mechanism is configured to construct single-word queries, multi-word queries, or both from the extracted words or phrases.

17. The computer system of claim 16, wherein while constructing the queries, the query formulation mechanism is further configured to apply one or more pre-determined logical combinations of the extracted words or phrases, thereby formulating queries based on a number of words or phrases with logical relationships.

18. The computer system of claim 16, wherein while extracting a set of words or phrases from each document, the first knowledge extraction mechanism is configured to extract a pre-determined number of words or phrases from the document.

19. The computer system of claim 13, further comprising a retrieval mechanism configured to retrieve a pre-determined number of results for each query.

20. The computer system of claim 13, wherein the receiving mechanism is further configured to receive a set of sensitive knowledge relevant to the documents;

wherein the piece of the second set of knowledge mapped to the document is also within the set of sensitive knowledge; and wherein while producing the mapping relationship, the mapping mechanism is configured to determine an intersection between the set of sensitive knowledge and the second set of knowledge.

21. The computer system of claim 13, wherein while producing the mapping relationship, the mapping mechanism is configured to present one or more words or phrases from the documents, which words or phrases correspond to the first set of knowledge, and one or more sensitive words or phrases extracted from the query results.

22. The computer system of claim 13, further comprising:

a ranking mechanism configured to determine a ratio of:

the number of results returned by a first query based on one or more words or phrases from the documents and one or more sensitive words or phrases, to the number of results returned by a second query based on one or more words or phrases from the documents; and a decision mechanism configured to determine an inference from the one or more words or phrases used to generate the first query based on the size of the ratio.

23. The computer system of claim 13, further comprising:

a reference selection mechanism configured to select the one or more reference corpora based on the documents, an intended audience, or both.

24. The computer system of claim 13, further comprising:

a detecting mechanism configured to detect one or more undesired inferences, wherein the undesired inferences are information intended to remain private, which can be extracted from a union of the document and the corpus and which cannot be extracted from the document or the corpus alone.

25. A computer-readable storage medium storing instructions that when executed by a computer cause the computer to perform a method for detecting inferences from documents, the method comprising:

receiving one or more documents;

extracting a first set of knowledge relevant to the documents;

formulating one or more queries to one or more reference corpora based on the first set of knowledge;

extracting a second set of knowledge from results received in response to the queries; and detecting an inference by producing a mapping relationship between at least one document and a piece of the second set of knowledge which is not within the first set of knowledge, wherein the mapping relationship indicates an inference from the documents.

* * * * *